United States Patent [19]

Watanabe et al.

[11] 4,374,056

[45] Feb. 15, 1983

[54] LOWLY IRRITATING DETERGENT

[75] Inventors: Hiroshi Watanabe, Funabashi; Hajime Hirota, Tokyo, both of Japan

[73] Assignee: Kao Soap Co., Ltd., Tokyo, Japan

[21] Appl. No.: 317,225

[22] Filed: Nov. 2, 1981

[30] Foreign Application Priority Data

Nov. 27, 1980 [JP] Japan ................................ 55-167156

[51] Int. Cl.$^3$ .................. C07C 103/44; C07C 103/50; C11D 1/10; C11D 1/94

[52] U.S. Cl. .................................... 252/546; 252/117; 252/153; 252/173; 252/DIG. 5; 252/DIG. 13; 252/DIG. 14; 424/70; 562/561; 562/564; 562/565

[58] Field of Search ............... 562/567, 568, 571, 561, 562/564, 565; 260/501.1; 252/117, 153, 173, 527, 546, DIG. 5, DIG. 13, DIG. 14; 424/70

[56] References Cited

U.S. PATENT DOCUMENTS

| | | | |
|---|---|---|---|
| 2,781,374 | 2/1957 | Mannheimer | 562/565 |
| 2,877,178 | 3/1959 | Bergman | 252/8.8 |
| 2,993,918 | 7/1961 | Mannheimer | 562/565 |
| 3,813,422 | 5/1974 | Marumo | 562/567 |
| 3,855,156 | 12/1974 | Marumo | 562/547 |
| 3,873,688 | 3/1975 | Kalopissis | 424/70 |
| 4,180,468 | 12/1979 | Tomidokoro | 252/117 |

FOREIGN PATENT DOCUMENTS

| | | | |
|---|---|---|---|
| 55-00336 | 1/1980 | Japan | 252/546 |
| 55-25436 | 2/1980 | Japan | 252/546 |
| 55-25458 | 2/1980 | Japan | 252/546 |

*Primary Examiner*—Dennis L. Albrecht
*Attorney, Agent, or Firm*—Flynn, Thiel, Boutell & Tanis

[57] ABSTRACT

A low irritating detergent composition comprises an amphoteric surface active agent of the amideamine type having the formula (1):

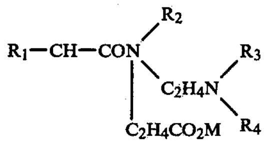

(1)

wherein $R_1$ is an alkyl or alkenyl group having 6 to 20 carbon atoms, $R_2$ is H, or $C_2H_4OH$, $R_3$ is H, $C_2H_4OH$ or $C_2H_4CO_2M$, $R_4$ is H, $C_2H_4OH$ or $C_2H_4CO_2M$, and M is H, an alkali metal, ammonium or organic ammonium, and mixing the amphteric surfactant of the formula (1) with one or more of another surfactants.

7 Claims, No Drawings

LOWLY IRRITATING DETERGENT

The present invention relates to a lowly irritating detergent. More particularly, the present invention relates to a detergent comprising a novel amide-amine type amphoteric surface active agent, which has a reduced irritating property to the skin or eye mucosa and is excellent in washing properties such as washing power and foaming power.

Detergents are essentially required to be excellent in the washing properties such as washing power and foaming power, and detergents which are brought into direct contact with the skin or the like, such as detergents for washing the body (for example, shampoos and body shampoos), dish washing detergents and light duty detergents for wool, are further required to have a reduced irritating property to the skin and eye mucosa.

As the surface active agent as the main ingredient of such detergent, there are used anionic surface active agents such as linear alkylbenzene-sulfonate salts (LAS), alkyl sulfate salts (AS), polyoxyethylene alkylether sulfate salts (ES) and α-olefin-sulfonic acid salts (AOS). These anionic surface active agents are good in the washing properties such as washing power and foaming power, but they are irritative to the skin and eye mocosa. Accordingly, it cannot be said that they are optimum main ingredients of detergents. Many proposals have heretofore been made to moderate this defect of the anionic surface active agents by using an amphoteric surface active agent, a nonionic surface active agent, a water-soluble polymeric compound or the like in combination with the anionic surface active agents. However, satisfactory reduction of the irritating property to the skin and the like cannot be attained by any of these proposals. When these auxiliary components are used alone, no satisfactory washing properties can be obtained.

We made researches with a view to developing a detergent having a reduced irritating property and good washing properties, and we found that a detergent comprising a novel amide-amine type amphoteric surface active agent has a reduced irritating property and good washing properties. We have now completed the present invention based on this finding.

More specifically, in accordance with the present invention, there is provided a lowly irritating detergent comprising an amide-amine type amphoteric surface active agent represented by the following general formula (1):

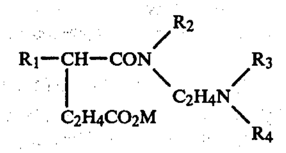
(1)

wherein $R_1$ stands for an alkyl or alkenyl group having 6 to 20 carbon atoms, $R_2$ stands for H or $C_2H_4OH$, $R_3$ stands for H, $C_2H_4OH$ or $C_2H_4CO_2M$, $R_4$ stands for H, $C_2H_4OH$ or $C_2H_4CO_2M$, and M stands for H, an alkali metal, ammonium or organic ammonium.

The amide-amine type amphoteric surface active agent that is used in the present invention is prepared by reacting a 2-alkyl-N-hydroxyethylimidazoline obtained by condensation of a fatty acid with aminoethylethanol amine, with an acrylic acid ester and saponifying the reaction product with an alkali.

The compound of this invention, represented by aforementioned general formula (1) can be produced by the following process: a process which comprises: reacting 1 mol of an imidazolin represented by the general formula (2):

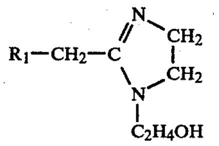
(2)

wherein $R_1$ is the same as in the general formula (1), with 1.0–5.0 mol of an acrylate ester at a reaction temperature of 40°–90° C. in a substantially anhydrous condition, thereby obtaining an intermediate represented by the general formula (3):

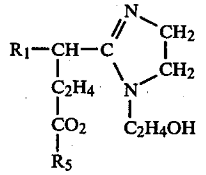
(3)

wherein $R_1$ has the same meaning as in the general formula 1, and $R_5$ represents a $C_1$–$C_4$ alkyl; adding to this intermediate, 1.0–5.0 mol of water and optionally an acrylate ester in portions, in a total amount not exceeding 5.0 mol; reacting the resulting mixture at a reaction temperature of 40°–90° C.; and saponifying the reaction product with an aqueous alkali solution. This process is described in further detail.

To 1 mol of an imidazoline represented by the general formula (2) is added 1.0–5.0 mol, preferably, 1.5–3.5 mol of an acrylate ester, and the mixture is reacted without addition of water, at a temperature of 40°–90° C., preferably, 50°–80° C. for a time of 0.5–6 hr., preferably, 2–4 hr. in a substantially anhydrous condition, thereby obtaining an intermediate represented by the general formula (3). Then, to this intermediate is added 1.0–5.0 mol, preferably, 1.5–2.5 mol of water, and the resulting mixture is reacted at a temperature of 40°–90° C., preferably, 60°–80° C. for a time of 1–7 hr., preferably, 2–4 hr., thereby opening the imidazoline ring and adding the acrylate ester present to the resulting amidoamine. The acrylate ester may be added all at a time at the start or may be added in portions, in such a manner that an amount required to add to an α position of the intermediate or an appropriate amount larger than that is added and then, the remaining portion of the ester together with water is added. The reaction product thus prepared is mixed with an alkali hydroxide usually in an equimolar amount to the acrylate ester, and the ester linkages derived from the acrylate ester are saponified at 40°–80° C., usually, 60°–70° C. for 2–3 hr. In this way, the novel amidoamine type compound having a carboxyethyl group in an α position, represented by the above general formula (1) is obtained.

Among the amide-amine type amphoteric surface active agents represented by the general formula (1), there are preferably used those in which $R_1$ stand for an alkyl group having 10 to 16 carbon atoms, $R_2$ stands for H or $—CH_2CH_2OH$, $R_3$ stands for $—CH_2CH_2OH$ or —$CH_2CH_2CO_2M$, $R_4$ stands for H or —$CH_2CH_2CO_2M$ and M stands for sodium.

The amide-amine type surface active agent of the present invention is incorporated into the detergent in an amount of 1 to 50% by weight, preferably 5 to 30% by weight.

In addition to the amide-amine type amphoteric surface active agent represented by the general formula (1), the lowly irritating detergent of the present invention may further comprise components described below, so far as the lowly irritating characteristic is not degraded.

Surfactants to be added to the composition of the invention includes conventional anionic surfactants, nonionic surfactants, cationic surfactants a amphoteric surfactants.

As the anionic surface active agent, the following compounds, for example, can be mentioned.

(1) Linear or branched alkylbenzene-sulfonate salts having an alkyl group having 10 to 16 carbon atoms on the average.

(2) Alkyl or alkenyl ethoxysulfate salts having a linear or branched alkyl or alkenyl group having 8 to 20 carbon atoms on the average and including 0.5 to 8 moles on the average of ethylene oxide added in the molecule.

(3) Alkyl or alkenyl sulfate salts having an alkyl or alkenyl group having 10 to 20 carbon atoms on the average (4) Olefin-sulfonic acid salts having 10 to 20 carbon atoms on the average in the molecule.

(5) Alkane-sulfonic acid salts having 10 to 20 carbon atoms on the average in the molecule.

(6) Saturated or unsaturated fatty acid salts having 10 to 20 carbon atoms on the average in the molecule.

(7) Alkyl or alkenyl ethoxycarboxylic acid salts having an alkyl or alkenyl group having 10 to 20 carbon atoms on the average and including 0.5 to 8 moles on the average of ethylene oxide added in the molecule.

(8) α-Sulfofatty acid salts or esters represented by the following formula:

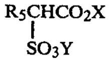

wherein X stands for an alkyl group having 1 to 3 carbon atoms or a counter ion of the anionic surface active agent, Y stands for a counter ion of the anionic surface agent, and $R_5$ stands for an alkyl or alkenyl group having 10 to 20 carbon atoms.

(9) Partially neutralized succinic acid derivatives represented by the following formula:

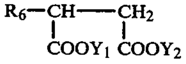

wherein $R_6$ stands for a saturated or unsaturated hydrocarbon group having 8 to 18 carbon atoms, and $Y_1$ and $Y_2$ stand for a hydrogen atom or a counter ion.

(10) Phosphoric ester type activating agents represented by the following formula:

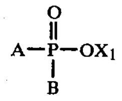

wherein A stands for

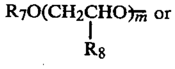 or 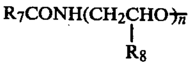

in which $R_7$ stands for a linear or branched saturated or unsaturated hydrocarbon group, $R_8$ stands for a hydrogen atom or a methyl group, m is a number of from 0 to 6 and B is a number of from 1 to 6, B stands for —$OX_2$ or A, and $X_1$ and $X_2$ stand for a hydrogen atom or a counter ion.

As the counter ion of the anionic surface active agent, there can be mentioned, for example, ions of alkali metals such as sodium and potassium, ions of alkaline earth metals such as calcium and magnesium, an ammonium ion, and salts of alkanol amines having 1 to 3 alkanol groups having 2 or 3 carbon atoms, such as monoethanol amine, diethanol amine, triethanol amine and tri-isopropanol amine.

As the nonionic surface active agent, for example, the following compounds can be mentioned.

(A) Polyoxyethylene alkyl or alkenyl ethers having an alkyl or alkenyl group having 8 to 20 carbon atoms on the average and including 3 to 12 moles of ethylene oxide added.

(B) Polyoxyethylene alkylphenyl ethers having an alkyl group having 8 to 12 carbon atoms on the average and including 3 to 12 moles of ethylene oxide added.

(C) Fatty acid alkanolamides represented by the following formula and alkylene oxide adducts thereof:

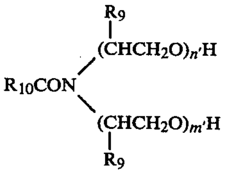

wherein $R_9$ stands for H or $CH_3$, $R_{10}$ stands for an alkyl or alkenyl group having 10 to 20 carbon atoms, n' is an integer of from 1 to 3, and m' is an integer of from 0 to 3.

(D) Polyoxypropylene alkyl or alkenyl ethers having an alkyl or alkenyl group having 10 to 20 carbon atoms on the average and including 1 to 20 moles of propylene oxide added.

(E) Polyoxybutylene alkyl or alkenyl ethers having an alkyl or alkenyl group having 10 to 20 carbon atoms on the average and including 1 to 20 moles of butylene oxide added.

(F) Nonionic activating agents having an alkyl or alkenyl group having 10 to 20 carbon atoms and including 1 to 30 moles of ethylene oxide and propylene oxide or ethylene oxide and butylene oxide (the ratio of ethylene oxide/propylene oxide or butylene oxide is in the range of from 0.1/9.9 to 9.9/0.1).

(G) Sucrose fatty acid esters comprising a fatty acid having 10 to 20 carbon atoms on the average and sucrose.

As the cationic surface active agent, for example, the following compounds can be mentioned.

(a) Di-long-chain-alkyl quaternary ammonium salts represented by the following formula:

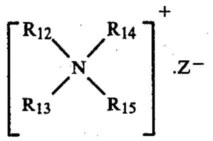

wherein $R_{12}$ and $R_{13}$ stand for an alkyl group having 10 to 26 carbon atoms, preferably 14 to 20 carbon atoms, $R_{14}$ and $R_{15}$ stand for an alkyl group having 1 to 5 carbon atoms, preferably 1 or 2 carbon atoms, and Z stands for a halogen atom, methyl sulfate or ethyl sulfate (the foregoing symbols have the same meanings hereinafter).

(b) Mono-long-chain-alkyl quaternary ammonium salts represented by the following formula:

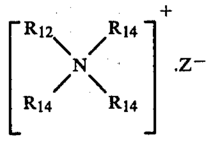

(c) Di-long-chain-alkyl polyoxyethylene quaternary ammonium salts represented by the following formula:

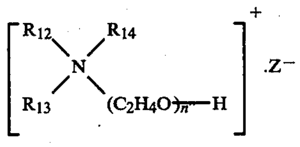

wherein n" is 1 to 20, preferably 1 to 10 (n" has the same meaning hereinafter), or

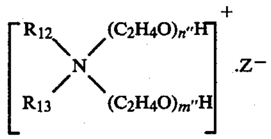

wherein m" is 1 to 20, preferably 1 to 10 (m" has the same meaning hereinafter).

(d) Mono-long-chain-alkyl polyoxyethylene quaternary ammonium salts represented by the following formula:

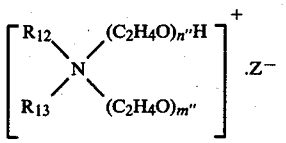

(e) Bis(hydroxyalkyl) quaternary ammonium salts represented by the following formula:

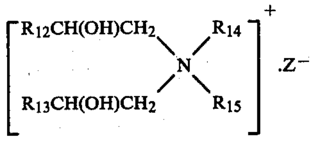

(f) Quaternary ammonium salts having an amide or ester linkage, such as compounds represented by the following formula:

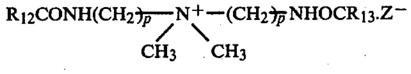

wherein p is 1 to 5, preferably 2 or 3 (p has the same meaning hereinafter), reaction products of

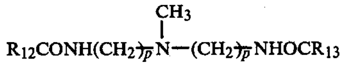
and
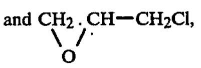, compounds represented by the following formula:

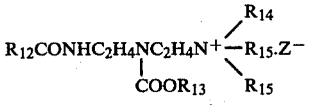

compounds represented by the following formula:

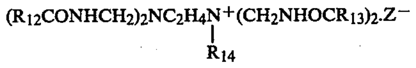

and compounds represented by the following formula:

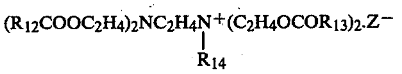

(g) Cationic polyamide compounds obtained by reacting 1 mole of diethylene triamine or dipropylene triamine with about 2 moles of a fatty acid having 12 to 24 carbon atoms, adding about 1 to about 2 moles of epichlorohydrin to the resulting condensate having an acid value smaller than 10, ring-opening polymerizing the adduct in the presence of an alkaline agent and neutralizing the product with a monobasic acid in an amount of 0.3 to 1.5 moles per mole of said amine.

(h) Di-quaternary salts such as compounds represented by the following formula:

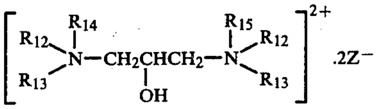

compounds represented by the following formula:

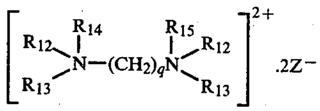

wherein q is a number of from 2 to 8 (q has the same meaning hereinafter), compounds represented by the following formula:

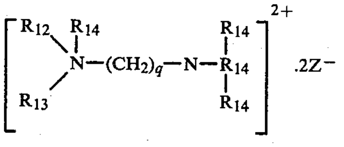

and compounds represented by the following formula:

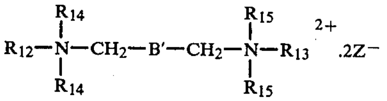

wherein B′ stands for a 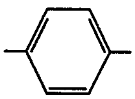 or $-CH=CH-$ residue.

As the amphoteric activating agent, for example, the following compounds can be mentioned.

(i) Alkylamine oxides represented by the following formula:

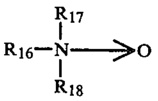

wherein $R_{16}$ stands for an alkyl or alkenyl group having 10 to 20 carbon atoms, and $R_{17}$ and $R_{18}$, which may be the same or different, stand for an alkyl group having 1 to 3 carbon atoms.

(ii) Compounds represented by the following formula:

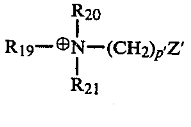

wherein $R_{19}$ stands for an alkyl or alkenyl group having 10 to 20 carbon atoms, $R_{20}$ and $R_{21}$ stand for an alkyl group having 1 to 4 carbon atoms, p′ is an integer of from 1 to 3, and Z′ stands for a group $-COO^{\ominus}$ or $-SO_3^{\ominus}$.

(iii) Imidazoline type amphoteric surface active agents represented by the following formula:

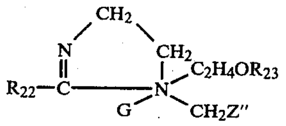

wherein $R_{22}$ stands for a fatty acid residue, $R_{23}$ stands for H, Na or $CH_2COOM'$, Z″ stands for COOM′, $CH_2COOM'$ or

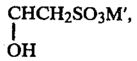

M′ stands for Na, H or an organic base, and G stands for OH, an acidic salt or an anionic surface active sulfate or sulfoxide. Viscosity-adjusting agents such as ethyl alcohol, glycerin, propylene glycol and inorganic salts, hydrotrop agents such as lower alkyl-benzene-sulfonic acid salts, urea and lower alkyl-sulfuric acid salts, perfumes, dyes, ultraviolet absorbers, antioxidants, antiseptic agents, appearance changing agents (for example, pearling agents), cationic polymers, nonionic polymers, other polymeric compounds and other ordinary detergent ingredients may be incorporated according to need.

The present invention will now be described in detail with reference to the following Examples that by no means limit the scope of the invention.

EXAMPLE 1

Various detergents having a composition shown in Table 1 were evaluated with respect to the foaming power, washing power and skin irritating property to obtain results shown in Table 1.

The properties were determined according to the following methods.

Washing Power Test (1)

A wool muslin cloth having a size of 5 cm×5 cm was uniformly coated with 0.4 ml of a chloroform solution containing 7% of hydrous lanolin and 0.005% of Sudan III and was then dried. The stained cloth was charged in a glass cylinder having a capacity of about 100 ml, which was filled with 40 ml of a solution containing 3% of a detergent, and was shaken for 15 minutes in a thermostat tank maintained at 40° C. Then, the cloth was sufficiently rensed in running water and dried. The reflectance was measured and the washing efficiency was calculated according to the following formula:

$$\text{Washing efficiency} = \frac{A - B}{C - B}$$

wherein A stands for the reflectance after washing, B stands for the reflectance before washing and C stands for the reflectance of the original cloth.

Washing Power Test (2) (Modification of Leanut Washing Power Test-JIS K-3370)

A slide glass was immersed for 1 to 2 seconds in a model soil comprising 20 g of an equal amount mixture of beef tallow and soy bean oil, 0.25 g of monoolein and 0.1 g Oil Red in 60 ml of chloroform, and the stained slide glass was air-dried and tested by a modified Leanut washing power tester. The detergent concentration in the test solution was 0.15%. The washing power was evaluated according to the standard described below by comparing the degree of removal of the stand with that obtained by using the following reference detergent composition.

Reference Detergent Solution 15 parts by weight of sodium alkylbenzene-sulfonate, 5 parts by weight of ethyl alcohol and 5 parts by weight were precisely weighed, and water was added to the mixture so that the total amount was 100 parts by weight. The pH value was adjusted to 7.0±0.5 by a sodium hydroxide solution (5%) or hydrochloric acid (1-6%).

Evaluation Standard

| | |
|---|---|
| apparently denser (apparently inferior) | −2 |
| slightly denser (slightly inferior) | −1 |
| no substantial difference | 0 |
| slightly lighter (apparently superior) | +1 |
| apparently lighter (apparently superior) | +2 |

Skin Irritating Property Test

A closed patch test was made on men for 24 hours as the skin irritating test. More specifically, adhesive plasters impregnated with a 0.2% aqueous solution of the surface active agent were applied to 26 men for 24 hours, and after 24 hours had passed from the point of removal of the plasters, the irritating property was evaluated. When definite red spots were observed, the irritating property was judged as being positive, and the irritating property was expressed by the positive ratio.

Foaming Power

The foaming power of a 0.5% aqueous solution of the detergent was tested according to the Ross-Miles test method.

TABLE 1

| | | Products of Present Invention | | | | | | Comparative Products | | | |
|---|---|---|---|---|---|---|---|---|---|---|---|
| | | 1 | 2 | 3 | 4 | 5 | 6 | 7 | 8 | 9 | 10 |
| 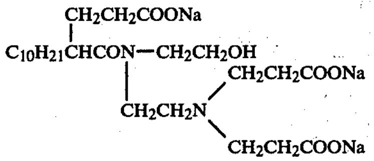 | (parts by weight) | 15 | — | — | 6 | 9 | 4 | — | — | — | — |
| 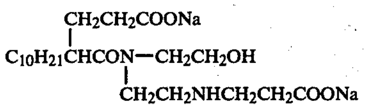 | (parts by weight) | — | 15 | — | 4 | 5 | 3 | — | — | — | — |
| 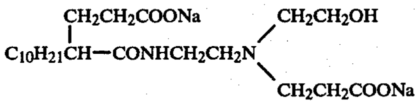 | (parts by weight) | — | — | 15 | 5 | 1 | 8 | — | — | — | — |
| $C_{12}H_{25}OSO_3Na$ | (parts by weight) | — | — | — | — | 2 | — | 10 | 2 | 1 | — |
| $C_{12}H_{25}O(CH_2CH_2O)_2SO_3Na$ | (parts by weight) | — | — | — | 3 | — | — | — | 13 | 14 | 15 |
| 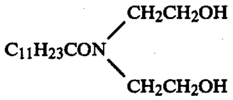 | (parts by weight) | 3 | 3 | 3 | 2 | 2 | — | 3 | 3 | — | 2 |
| 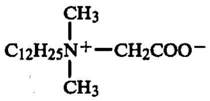 | (parts by weight) | — | — | — | — | — | 3 | — | — | 3 | 2 |
| Deionized water | (parts by weight) | 82 | 82 | 82 | 80 | 81 | 82 | 87 | 82 | 82 | 81 |
| Skin Irritating Property positive ratio, (%) | | 0 | 3.8 | 3.8 | 3.8 | 3.8 | 0 | 42.3 | 38.5 | 38.5 | 46.2 |
| Property Tests | | | | | | | | | | | |
| Foaming Power (mm) | | 185 | 190 | 200 | 215 | 230 | 190 | 240 | 230 | 230 | 210 |
| Washing Power Test (1) (%) | | 62 | 59 | 67 | 69 | 64 | 61 | 62 | 65 | 68 | 68 |
| Washing Power Test (2) (modified Leanut test method) | | 0 | +1 | 0 | +1 | +1 | +1 | +1 | +1 | 0 | +1 |

EXAMPLE 2

The amide-amine type surface active agents of the present invention were compared with anionic surface active agents customarily used as starting materials of detergents with respect to the foaming power and the effect on washed hairs. The obtained results are shown in Table 2.

(1) Foaming Power

The foaming power of a 0.5% aqueous solution of the detergent was tested according to the Ross-Miles test method.

(2) Combing Force 30 g of a tress of human hairs was washed for 1 minute with 10 ml of a 0.5% aqueous solution of the surface active agent (40° C.), and then, it was rinsed with running water and drained. The tress was set at a strain gauge and the force required for combing out the tress from the root to tip was measured ("wet state"). The tress which had been rinsed with running water and drained was dried by a blow-drier and allowed to stand still in a thermostat chamber maintained at a temperature of 25° C. and a relative humidity of 65% overnight. The tress was set at a strain gauge and the force required for combing out the tress from the root to tip was measured ("dry state"). Incidentally, the measurement was conducted 50 times and the average value was calculated.

Incidentally, the smaller is the force value, the better is the combing property.

TABLE 2

| Surface Active Agent | | Bubbling Power (mm) | Combing Force (g) set state | Combing Force (g) dry state |
|---|---|---|---|---|
| R—$OSO_3Na$ | (R = lauryl) | 230 | 327 | 195 |
| R—$OSO_3TEA$ | (R = lauryl) | 210 | 308 | 181 |
| R—$O(CH_2CH_2O)_nSO_3Na$ | (R = lauryl, n = 3 on average) | 195 | 335 | 226 |
| R—$O(CH_2CH_2O)_nSO_3Na$ | (R = lauryl, n = 2 on average) | 225 | 331 | 207 |
| 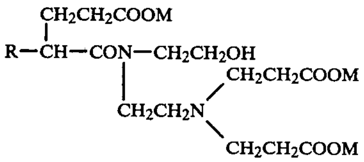 | (R = lauryl, M = Na) | 180 | 321 | 93 |
| 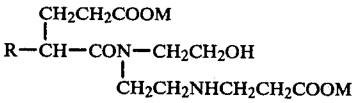 | (R = lauryl, M = Na) | 185 | 311 | 89 |
| 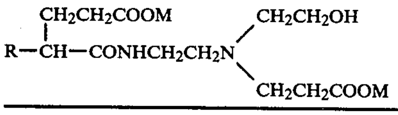 | (R = lauryl, M = Na) | 190 | 306 | 81 |

EXAMPLE 3

Each of the following shampoo, light duty detergent for wool and dish washing detergent was very low in the skin irritating property and had good washing properties.

| Shampoo: | |
|---|---|
| 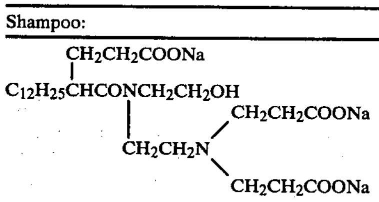 | 7.5% by weight |
| 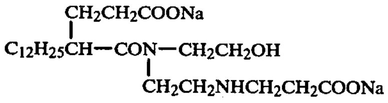 | 3.9% by weight |
| 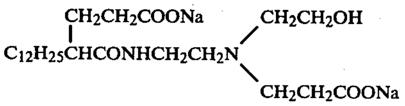 | 3.6% by weight |
| Sodium polyoxyethylene (2.0) | 3.0% by weight |

-continued

| | |
|---|---|
| alkyl (average carbon number = 12) ether sulfate | |
| Lauryl diethanolamide | 3.0% by weight |
| Perfume and dye | appropriate amounts |
| Water | balance |
| Total | 100% by weight (pH value = 7.2) |

| Light Duty Detergent for Wool: | |
|---|---|
| 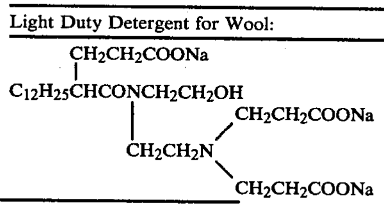 | 10% by weight |
| $C_{12}H_{25}(CH_3)_2$——>O | 5% by weight |
| Ethyl alcohol | 8% by weight |
| Perfume | appropriate amount |
| Water | 77% by weight |

| Dish Washing Detergent: | |
|---|---|
| 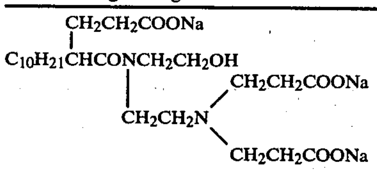 | 15% by weight |
| Sodium α-olefin-sulfonate (average carbon number = 12) | 5% by weight |
| Lauryl diethanolamide | 5% by weight |
| Ethyl alcohol | 8% by weight |
| Perfume, dye and opacifying agent | appropriate amounts |
| Water | balance |
| Total | 100% by weight |

The embodiments of the invention in which an exclusive property or privilege is claimed are defined as follows:

1. A detergent comprising an amide-amine type amphoteric surface active agent represented by the following general formula (1):

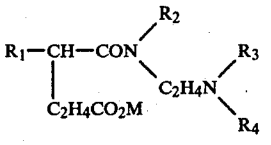
(1)

wherein $R_1$ stands for an alkyl or alkenyl group having 6 to 20 carbon atoms, $R_2$ stands for H or $C_2H_4OH$, $R_3$ and $R_4$ are each H, $C_2H_4OH$, or $C_2H_4CO_2M$, and M stands for H, an alkali metal, ammonium or organic ammonium.

2. A detergent as set forth in claim 1, wherein $R_1$ of the general formula (1) stands for an alkyl group having 10 to 16 carbon atoms.

3. A detergent as set forth in claim 1 or 2, wherein $R_2$ of the general formula (1) stands for H or $-CH_2CH_2OH$.

4. A detergent as set forth in claim 1 or claim 2, wherein $R_3$ of the general formula (1) stands for $-CH_2CH_2OH$ or $-CH_2CH_2CO_2M$.

5. A detergent as set forth in claim 1 or claim 2, wherein $R_4$ of the general formula (1) stands for H or $-CH_2CH_2CO_2M$.

6. A detergent as set forth in claim 1 or claim 2, wherein the content of the amide-amine type amphoteric surface active agent is 1 to 50% by weight.

7. A detergent as set forth in claim 6, which further comprises one or more of anionic, cationic, nonionic and amphoteric surfactants.

* * * * *